(12) United States Patent
Kubo et al.

(10) Patent No.: US 6,569,907 B1
(45) Date of Patent: May 27, 2003

(54) HEAT TRANSPIRATION PREPARATION AND METHOD OF THE HEAT TRANSPIRATION OF CHEMICAL BY USING THE SAME

(75) Inventors: Nobuya Kubo, Hyogo (JP); Shusaku Tsutsumi, Hyogo (JP); Kouichi Takata, Hyogo (JP); Takahiro Hasegawa, Hyogo (JP)

(73) Assignee: Earth Chemical Co., Ltd., Tokyo (JP)

( * ) Notice: Subject to any disclaimer, the term of this patent is extended or adjusted under 35 U.S.C. 154(b) by 0 days.

(21) Appl. No.: 09/646,451

(22) PCT Filed: Dec. 20, 1999

(86) PCT No.: PCT/JP99/07133

§ 371 (c)(1),
(2), (4) Date: Sep. 12, 2000

(87) PCT Pub. No.: WO00/42117

PCT Pub. Date: Jul. 20, 2000

(30) Foreign Application Priority Data

Jan. 14, 1999 (JP) ............................................. 11-8109

(51) Int. Cl.⁷ .................... A01N 25/18; A24F 25/00; A61K 7/46; A61L 9/04; C09K 3/30
(52) U.S. Cl. ................. 516/4; 222/4; 239/60; 422/5; 424/76.3; 424/76.4; 428/905; 512/4
(58) Field of Search ............................ 516/4; 424/76.3, 424/76.4; 222/4; 239/60; 422/5; 428/905; 512/4

(56) References Cited

U.S. PATENT DOCUMENTS

RE16,495 E * 12/1926 Bradner
3,567,119 A * 3/1971 Wilbert et al. ............ 239/60 X
3,948,445 A * 4/1976 Andeweg ................... 239/60 X
4,663,315 A * 5/1987 Hasegawa et al.
4,781,895 A * 11/1988 Spector ....................... 422/5 X
5,419,879 A * 5/1995 Vlahakis et al. ............. 422/5 X
5,477,640 A * 12/1995 Holtkamp, Jr. ........... 239/60 X
5,575,992 A * 11/1996 Kunze ........................ 424/76.4
5,593,635 A * 1/1997 Matsumoto et al. ........... 422/5
5,891,400 A * 4/1999 Ansari et al. .......... 424/76.4 X
6,413,476 B1 * 7/2002 Barnhart .................... 422/5 X

FOREIGN PATENT DOCUMENTS

| JP | 51-30127 | 8/1976 |
| JP | 11-349405 | 12/1999 |
| WO | 98/35552 | 2/1998 |

OTHER PUBLICATIONS

Chemical Engineers' Handbook, Fifth Edition, Edited By R.H. Perry et al., p. 18–82, 1980.*
XP–002171346—Abstract (Feb. 1981).
European Search Report dated Jul. 17, 2001.
International Search Report Mar. 21, 2000.

* cited by examiner

*Primary Examiner*—Richard D. Lovering
(74) *Attorney, Agent, or Firm*—Sughrue Mion, PLLC

(57) ABSTRACT

To provide thermal evaporation preparations and a method of thermal evaporating chemicals whereby the chemicals can be efficiently evaporated. Thermal evaporation preparations, wherein the preparation is in the form of a solid at ordinary temperature but molten by heating into a liquid as a whole, and a chemical employed as the active ingredient is evaporated from the ingredients of the preparation thus liquefied by heating, and a method of thermal evaporating chemicals.

9 Claims, 5 Drawing Sheets

HEAT TRANSPIRATION PREPARATION AND METHOD OF THE HEAT TRANSPIRATION OF CHEMICAL BY USING THE SAME

This application is a 371 of PCT/JP 99/07133 filed Dec. 20, 1999.

TECHNICAL FIELD

This invention relates to thermal evaporation preparations (sometimes, called heat vaporizing preparations) and a method of thermal evaporation of chemicals thereof. More particularly, it relates to thermal evaporation preparations which are usable appropriately in vehicles such as automobiles, airplanes and trains or in rooms equipped with metal goods, ornamental plants, etc. and a method of thermal evaporation of chemicals.

BACKGROUND ART

Thermal evaporation preparations have been employed to exterminating (harmful) insect pests from human housing facilities such as houses and buildings.

These thermal evaporation preparations are advantageous in that chemicals such as insecticidal ingredients can be evaporated into the atmosphere at once by taking advantage of a chemical exothermic reaction system thereby enabling the extermination of (harmful) insect pests while saving labor.

It has been well-known to use foaming agents in these thermal evaporation preparations so as to accelerate the evaporation of chemicals.

For example, there has been well-known an insect pest controlling method wherein a mixture of an insecticide with azodicarbonamide (i.e., a foaming agent) is heated to thereby decompose the foaming agent and the chemical is fumed with the use of the gas thus evolved as the decomposition product (JP-B-58-42841; the term "JP-B" as used herein means an "examined Japanese patent publication").

With the recent diversification in housing spaces and living environment, it has been required to further improve the evaporability of the chemicals employed as the active ingredients.

In the conventional thermal evaporation preparations with the use of the hydroexothermic system (i.e., the exothermic system due to addition of water) on the other hand, it is sometimes observed that the exothermic reaction per se fails to occur and thus the chemicals cannot be evaporated or the evaporation of the chemicals becomes unstable due to the unstable supply of water (i.e., excessive or insufficient water supply) to hydroexothermic substances.

In addition, some preparations make metal goods, electrical wiring, etc. rusty or exert undesirable effects on ornamental plants. Therefore, these preparations must be cautiously used particularly in vehicles (automobiles, etc.) and places equipped with many metal goods.

Accordingly, an object of the present invention is to provide thermal evaporation preparations and a method of thermal evaporating chemicals as will be described hereinbelow:

thermal evaporation preparations which are usable appropriately in vehicles such as automobiles, airplanes and trains or in rooms equipped with metal goods, ornamental plants, etc;

a method of thermal evaporating chemicals whereby the chemicals can be efficiently evaporated; and a method of thermal evaporating chemicals which is usable appropriately in vehicles such as automobiles, airplanes and trains or in rooms equipped with metal goods, ornamental plants, etc.

DISCLOSURE OF THE INVENTION

According to the present invention, the above-mentioned object of the present invention can be achieved by the thermal evaporation preparations and a method of thermal evaporating chemicals as will be described hereinbelow.

(1) A thermal evaporation preparation, wherein the preparation is in the form of a solid at ordinary temperature but molten by heating into a liquid as a whole, and a chemical employed as the active ingredient is evaporated from the ingredients of the preparation thus liquefied by heating.

(2) The thermal evaporation preparation as described in the above (1), wherein from the above-described preparation liquefied by heating, particles having a median particle diameter ($\mu$) of 1 to 2 $\mu$m and an evaporated particle diameter distribution giving $\mu+\alpha$ (wherein $\alpha$ represents the standard deviation) of $4\mu$ (i.e., 4 times as much as the median particle diameter) and $\mu-\alpha$ of $\frac{1}{4}\mu$ (i.e., ¼ times as much as the median particle diameter) are evaporated.

(3) The thermal evaporation preparation as described in the above (1) or (2), wherein all of the ingredients of the preparation have each a melting point falling within a range of from 50 to 300° C.

(4) A method of thermal evaporating a chemical comprising the following steps:

the step of heating the thermal evaporation preparation as described in any of the above (1) to (3) with a heating means and melting the preparation into a liquid as a whole; and the step of evaporating a chemical employed as the active ingredient from the ingredients of the thus liquefied preparation.

(5) The method of thermal evaporating a chemical as described in the above (4), wherein the step of evaporating a chemical is one in which the chemical used as the active ingredient is evaporated from the ingredients of the above-described liquefied preparation as particles having a median particle diameter ($\mu$) of 1 to 2 $\mu$m and an evaporated particle diameter distribution giving $\mu+\alpha$ (wherein $\alpha$ represents the standard deviation) of $4\mu$ (i.e., 4 times as much as the median particle diameter) and $\mu-\alpha$ of $\frac{1}{4}\mu$ (i.e., ¼ times as much as the median particle diameter).

(6) The method of thermal evaporating a chemical as described in the above (4) or (5), wherein the above-described heating means is a means with the use of heat evolution caused by a hydroexothermic reaction between a hydroexothermic substance and a liquid for the hydroexothermic reaction.

(7) A method of thermal evaporating a chemical in which a thermal evaporation preparation is heated by using heat evolved by a hydroexothermic reaction between a hydroexothermic substance and a liquid for the hydroexothermic reaction to thereby evaporate the chemical used as the active ingredient in the preparation, wherein the liquid for the hydroexothermic reaction is supplied so as to be capable of elevating the temperature at the part to be heated to 300° C. or more within 100 seconds after the initiation of water absorption by the hydroexothermic substance.

(8) The method of thermal evaporating a chemical as described in the above (7), wherein the liquid for the hydroexothermic reaction comprises a liquid stabilizer capable of elevating the temperature at the part to be heated to 300° C. or more within 100 seconds after the initiation of water absorption by the hydroexothermic substance.

(9) The method of thermal evaporating a chemical as described in the above (8), wherein the liquid stabilizer is at least one member selected form the group consisting of alcohols, benzethonium chloride, benzalkonium chloride, sucrose, alkyldiaminoethylglycine hydrochloride, chlorohexidine gluconate, cetylpyridinium chloride, sodium lauryl sulfate, sodium dehydroacetate, chlorinated isocyanuric acid and refined chloride of lime.

Next, the present invention will be illustrated.

The thermal evaporation preparation according to the present invention has characteristics that it is in the form of a solid at ordinary temperature but molten by heating into a liquid as the whole preparation and that a chemical contained as the active ingredient in the thus liquefied preparation is evaporated into the atmosphere.

Thus, the thermal evaporation preparation of the present invention involves those composed exclusively of ingredients which are each in the form of a solid at ordinary temperature but molten into a liquid by heating and those wherein at least a part of the ingredients are molten into a liquid by heating and thus the whole preparation is liquefied in the course of heating.

The heating time may be appropriately determined so as to liquefy the whole preparation. From the viewpoint of convenience, it is preferable that the heating is completed, for example, within 10 minutes, more preferably within 5 minutes and most preferably for 2 to 3 minutes.

It is preferable that the thermal evaporation preparation of the present invention is one which is molten by heating into a homogeneous liquid composed of all of the ingredients of the preparation. That is to say, it is preferable that all of the ingredients of the thermal evaporation preparation have each a melting point falling within a range of from 50 to 300° C., provided that liquid ingredients and those having no melting point (undergoing decomposition, vaporization, etc.) are excluded from this category.

In the present invention, the thermal evaporation preparation is liquefied by heating as described above so that the heat can be uniformly transferred and the evaporation of the chemical can be sufficiently enhanced.

The term "is molten" as used herein means that the whole preparation turns from a solid into a liquid. A solid preparation impregnated with a liquid chemical and supported with the same is also included in the scope of the present invention, so long as the whole preparation can be liquefied by heating. Moreover, the term "liquid" as used herein means fluids involving sols and gels.

The thermal evaporation preparation of the present invention is in the form of a solid at ordinary temperature. The term "ordinary temperature" means a temperature of lower than 50° C. The term "solid" means a substance having no fluidity. Therefore, a preparation having no fluidity as a whole is regarded as a solid herein, even though it partly contains a liquid (for example, one impregnated and supported with a liquid).

Since the thermal evaporation preparation of the present invention is in the form of a solid at ordinary temperature, it can be easily handled in storage or distribution and the chemical can be maintained in a stable state.

The melting temperature at which the thermal evaporation preparation according to the present invention is molten into a liquid as a whole preferably ranges from 50 to 300° C., more preferably from 60 to 100° C., though the present invention is not restricted to the above temperature range so long as the whole preparation can be liquefied. The melting temperature is appropriately determined depending on the ingredients, production method, etc. of the preparation.

It is not favorable that the preparation is molten into a liquid at a temperature much exceeding 300° C. (for example, at 500° C.), since handling at such a high temperature might cause some problem in safety.

It is preferable that the thermal evaporation preparation of the present invention is heated to a temperature higher than the melting point of the preparation as described above. In the case of a preparation having a melting temperature of 250° C., for example, it may be heated to about 300 to 400° C. so as to efficiently and surely liquefy the whole preparation.

When the thermal evaporation preparation according to the present invention is to be used in vehicles such as automobiles, airplanes and trains or in rooms equipped with metal goods, ornamental plants, etc., it is preferable that no acidic gas is evolved from the thermal evaporation preparation by the heating as described above. More particularly speaking, it should be avoided to employ, as the ingredients of the thermal evaporation preparation of the present invention, compounds evolving such acidic gases as exerting undesirable effects, both in concentration or type, upon decomposition or evaporation by heating. However, such compounds exerting undesirable effects may be employed in the present invention so long as they have decomposition temperature exceeding the above-described heating temperature.

In the present invention, the thus liquefied preparation is heated to, for example, 200 to 400° C. (preferably 300 to 400° C.) to thereby evaporate the chemical employed as the active ingredient from the preparation.

By evaporating the chemical from the thus liquefied preparation by heating, the evaporation efficiency can be improved. This is seemingly because the evaporated particles containing the chemical would have characteristics enabling efficient evaporation. More particularly speaking, it is favorable that particles having a median particle diameter ($\mu$) of 1 to 2 $\mu$m and an evaporated particle diameter distribution giving $\mu+\alpha$ of $4\mu$ (i.e., 4 times as much as the median particle diameter) and $\mu-\alpha$ of $\frac{1}{4}\mu$ (i.e., ¼ times as much as the median particle diameter) are evaporated, wherein $\alpha$ represents the standard deviation while $\mu+\alpha$ and $\mu-\alpha$ each represents an inflection point. Preparations having such a particle diameter distribution are appropriate for bactericidal, mildew-proofing, deodorant and aromatic products.

The thermal evaporation preparation according to the present invention may be in the form of, for example, granules, powders, dusts, blocks or tablets.

Among all, granular preparations are preferable, since they have excellent heat conductivity and improved heat melting properties and are not scattered or leaked during distribution. The particle size (diameter) of the granules ranges from, for example, 0.5 to 5 mm, preferably from 1 to 3 mm.

Examples of the preparation of the present invention having the above-described characteristics involve preparations obtained by merely binding solid chemicals, those wherein a solid carrier is impregnated and supported with a liquid chemical and those obtained by solidifying a liquid chemical by adding a solidifier thereto.

The thermal evaporation preparation according to the present invention can be obtained by, for example, homogeneously mixing a chemical with a binder and molding the mixture into a desired shape.

A granular preparation can be obtained by, for example, homogeneously mixing plural chemicals with binders such as hydroxypropyl cellulose, hydroxypropylmethyl cellulose, starch, polyvinylalcohol, polyvinylacetate, etc., then adding water, kneading the resultant mixture and molding it with a granulating machine, etc. followed by drying.

It is preferable that the thermal evaporation preparation of the present invention further contains a saccharide so as to enhance the strength of the preparation and enhance the evaporability of the chemical, i.e., the active ingredient without inhibiting the melting. The content of the saccharide in the preparation ranges, for example, from 5 to 50% by weight. When the content of the saccharide is excessively large, there arise some unfavorable phenomena such as the evolution of a scorching smell at the evaporation or a decrease in the vaporization ratio. When the content of the saccharide is excessively small, on the other hand, the preparation becomes sticky due to a decrease in the strength and cakes in some cases (for example, granular preparations).

Examples of the saccharide include monosaccharide (glucose, sorbitol, etc.), disaccharides (sucrose, etc.) oligosaccharides and polysaccharides (starch, etc.). Among these saccharides, it is preferable to use monosaccharides since they can be easily molten and promote smooth evaporation of the chemical when used in the preparation.

As the chemical to be employed as the active ingredient in the thermal evaporation preparation according to the present invention, use can be made of those which can be evaporated from the preparation liquefied by heating as described above. Examples thereof include insecticides, insect repellents, mothproofing agents, mildewproofing agents, bactericides, deodorizers and aromatic agents (i.e., perfumes).

Furthermore, use can be made of surfactants, solubilizing aids, antioxidants, stabilizers, synergists, UV absorbers, coloring matters, various solvents, etc. in addition to the active ingredient as described above, so long as the present invention can be embodied. As stated above, it is preferable that these ingredients of the preparation have each a melting point falling within a range of from 50 to 300° C.

As the insecticides, use can be made of pyrethroid insecticides, organophosphorus ones and carbamate ones.

Examples of the pyrethroid insecticides include furamethrin, cyphenothrin, phenothrin, permethrin, allethrin, phthalthrin, empenthrin, tefluthrin, prallethrin, imiprothrin, transfluthrin, pyrethrin, dl d-T80-allethrin, d-T80-phthalthrin, d-T80-resmethrin, d-T80-furamethrin and tralomethrin.

Examples of the organophosphorus insecticides include fenitrothion, chlorpyrifos, malathion, dichlorvos, pyridaphenthion and trichlorphon.

Examples of the carbamate insecticides include carbaryl, benfuracarb, propoxur and methoxadiazone.

As the insecticides, furthermore, use can be made of insect hormone agents and antihormone agents, for example, insect juvenile hormone agents (methoprene, etc.), antijuvenile hormone agents (precocene, etc.) and molting hormone agents (ecdysone, etc.), fibronil and sulfuramide.

Other examples of the insecticides usable in the present invention include essential oils of Japanese cypress, cedar and white cedar, menthol, Amur cork extract, citrus peel and seed extracts, aromatic sulfonamide derivatives, isopropyl 4,4'-dibromobenzilate, 2,3-dihydro-2,2-dimethyl-7-benzo [b]furanyl-N-dibutylaminothio-N-methyl carbamate, silane compounds, cinnamic acid derivatives, cinnamyl acetate, isoprothiolane, p-hydroxybenzoates, iodinated formal, phenols, phthalates, 3-bromo-2,3-iodo-2-propenyl-ethyl carbonate, monoterpene based ketones, monoterpene based aldehydes, monoterpene based epoxides, benzyl salicylate and phenyl salicylate.

Examples of the insect repellents and the mothproofing agents include 2,3,4,5-bis(δ-butylene)-tetrahydrofurfural, N,N-diethyl-m-toluamide, di-n-propyl isocinchomeronate, di-n-butylacetic acid, 2-hydroxyethyloctylsulfuric acid, 2-t-butyl-4-hydroxyanisole, 3-t-butyl-4-hydroxyanisole, cycloheximide, β-nitrostyrene cyanoacrylonitrile, trinitrobenzene/aniline complex and naphthalene.

Examples of the bactericides and mildewproofing agents include 2,4,4'-trichloro-2'-hydroxydiphenyl ether, 2,3,5,6-tetrachloro-4-(methylsulfonyl)pyridine, alkylbenzylmethylammonium chlorides, benzylmethyl-{2-[2-(p-1,1,3,3-tetramethylbutylphenoxy)ethoxy]ethyl}ammonium chloride, 4-isopropyltropolone, N, N-dimethyl-N'-phenyl-N'-(fluorodichloromethylthio)sulfonamide, 2-(4'-thiazolyl) benzimidazole, N-(fluorodichloromethylthio)-phthalimide, 6-acetoxy-2,4-dimethyl-m-dioxin, isopropylmethylphenol, o-phenylphenol, p-chloro-m-xylenol, butylparaben, methylparaben, ethylparaben, propylparaben, α-bromocinnamaldehyde, thiabendazole, 3-iodo-2-propenylbutyl carbamate, benzoic acid, sorbic acid, triclosan, N,N-dimethyl-N'-(fluorodichloromethylthio)-N"-phenylsulfuramide, N-dichlorofluoromethylthio-N',N'-dimethyl-N-p-tolylsulfuramide, α-[2-(4-chlorophenyl) ethyl]-α-(1,1-dimethylethyl)-1H-1,2,4-triazole-1-ethanol, hinokitiol and thymol.

Examples of the deodorizers include lauryl methacrylate, methylated cyclodextrin and zinc chloride.

Examples of the aromatic agents (i.e., the perfumes) include rush and Japanese cypress essential oil ingredients, citronella, citronel, citronellal, lemon, lemon grass, orange, eucalyptus and lavender.

Examples of rust preventives include 1,2, 3-benzotriazole (for copper) and dicyclohexylammonium nitrite (for steel).

Either one of these active ingredients or a combination of two or more thereof may be used.

Such a chemical serving as the active ingredient may be used in the preparation preferably in an amount of from 5 to 90% by weight, more preferably from 5 to 50% by weight.

If needed, the preparation may further contain effectiveness increasing agents (piperonylbutoxide, N-propylisome, Synepirin 222, Synepirin 500, Lethan 384, Lethan S-421, etc.), evaporability improvers (phenyl isothiocyanate, high-mix acid dimethyl esters, etc.), etc.

The thermal evaporation preparation according to the present invention makes it possible to efficiently evaporate the chemical serving as the active ingredient into the target space without exerting any undesirable effect on metal goods or ornamental plants during the evaporation.

Next, a typical example of the thermal evaporation preparation of the present invention for exerting mildew-proofing, bactericidal and deodorizing effects on automobiles will be shown, though the present invention is not restricted thereto:

|  | part by weight |
|---|---|
| Active ingredient (at least one member selected from mildew-proofing agents, bactericides and deodorizers) | 1 to 90 |
| Binder | 0.1 to 10 |
| Perfume | 0 to 10 |
| Saccharide | 0.1 to 50 |

(in the above composition, the saccharide may be also served as a binder).

The thermal evaporation preparation thus obtained may be packed in a vessel made of, for example, plastics, paper, metals, ceramics or glass.

To heat the thermal evaporation preparation of the present invention, use is made of a means/method whereby the preparation can be conveniently heated to a temperature range enabling the liquefaction of the above-described preparation as a whole and the evaporation of the chemical (i.e., from 200 to 400° C., preferably from 300 to 400° C.), for example, a hydroexothermic system, an air oxidation heating system, an electrical heating system or a platinum catalyst system.

In the above-described hydroexothermic system, a hydroexothermic substance which undergoes an exothermic reaction when water is added thereto is employed. Examples of the hydroexothermic substance include calcium oxide, magnesium chloride, aluminum chloride, calcium chloride and iron chloride. Among all, calcium oxide is preferable therefor and one having a grain size of 1 to 20-mesh is favorable. When brought into contact with water, calcium oxide having a grain size falling within the range as specified above can evolve heat to give the temperature as described above (i.e., a temperature at which the active ingredient can be well evaporated to achieve the objects of the present invention, for example, 300 to 400° C.) When the grain size is excluded from the range as specified above, in contrast, temperature cannot be elevated to the above level and thus the desired effects cannot be achieved in some cases. As a matter of course, the heating temperature of the above hydroexothermic substance varies depending on the amount of water to be brought into contact therewith. It is therefore generally preferable to use about 1 to 3 mol of water per mol of calcium oxide. The amount of calcium oxide may be regulated, if necessary.

To control the heat value evolved by the calcium oxide, it is also possible to further add, as another exothermic substance, a clay mineral (diatomaceous earth, acid clay, zeolite, etc.) to calcium oxide.

In the air oxidation heating system as described above, use is made of a metal or a metal compound which evolves heat in an oxidation reaction. Examples thereof include a method wherein a mixture of an iron powder with an oxidizing agent (ammonium chlorate, etc.), a mixture of iron with potassium sulfate, iron sulfate or a metal chloride is brought into contact with oxygen and water and a method wherein a mixture of sodium sulfide with iron carbide is brought into contact with oxygen.

Examples of the above-described electrical heating system (means) include nichrome wires, positive thermistor controllers (PTC) and heaters such as sheet heaters and semiconductor heaters. When the thermal evaporation preparation according to the present invention is heated by the electrical heating system, it is preferable that the heating rate attains the maximum level within 5 minutes (more preferably 3 minutes) after the initiation of heating. By heating the preparation in such a heating pattern, the chemical can be rapidly, uniformly and efficiently diffused. The expression "the maximum level of the heating rate" means that the temperature is elevated at the highest level in a unit time. More particularly speaking, the heating rate preferably ranges from 40° C./min to 450° C./min, more preferably form 50° C./min to 400° C./min. In this system, it is preferable that the thermal evaporation preparation is heated while not being in contact with the electrical heating means.

In the present invention, it is favorable to employ the hydroexothermic system as the heating means, since it can be simply performed and a high temperature can be easily established thereby.

The thermal evaporation preparation according to the present invention may be indirectly heated by using such a heating means. Namely, the thermal evaporation preparation contained in a vessel can be heated by the heating means located outside the vessel.

Now, a mode of the utilization of the thermal evaporation preparation of the present invention with the use of the hydroexothermic system, i.e., a preferable embodiment thereof, will be described.

In the present invention, use can be made of a device for thermal evaporation of the chemical consisting of, in a top open vessel;

a container having therein a liquid for hydroexothermic reaction to be reacted with an exothermic substance in the above-described hydroexothermic system; and a container having the thermal evaporation preparation of the present invention; and an exothermic substance provided outside the container having the preparation therein.

Owing to this constitution, the above-described exothermic substance is reacted with the liquid for hydroexothermic reaction and thus heat is evolved. Thus, the whole preparation can be heated (preferably to 50 to 300° C.) so that it is molten into a liquid by the heat and the chemical serving as the active ingredient is evaporated from the ingredients of the thus liquefied preparation.

It is favorable that the device involves the liquid for hydroexothermic reaction, since such a device can be used even in the absence of water and the exothermic substance can be reacted continuously with water in a definite amount appropriate for the exothermic reaction. As the liquid for hydroexothermic reaction, use may be made of water optionally containing various additives. These additives are those which neither prevent the evaporation of the chemical nor lower the reactivity of water with the exothermic substance. Examples thereof include organic solvents and liquid stabilizers.

As the results of the inventors' studies, it is clarified that the following requirement should be satisfied to achieve favorable thermal evaporation by the hydroexothermic system with the use of the liquid for reaction.

When the hydroexothermic substance is treated with the liquid for reaction and the chemical is evaporated with the use of the heat thus evolved, the chemical can be well evaporated by quickly heating the part to be heated of the vessel containing the chemical.

More particularly speaking, it is preferable in the present invention that the liquid for hydroexothermic reaction (hereinafter referred to as the reaction liquid) is supplied so that the temperature of the part to be heated is elevated as quickly as possible and thus the temperature attains 300° C. or more within 100 seconds after the initiation of the absorption of water by the hydroexothermic substance. To quickly perform the hydroexothermic reaction, it is preferable that the reaction liquid (in particular, water) in the reaction equivalent amount is supplied within 3 minutes, more preferably 1 minute, to the hydroexothermic substance.

To satisfy the above-described requirement, it is preferable to employ a structure wherein the reaction liquid can be quickly reach the hydroexothermic substance from the container of the reaction liquid. For example, it is favorable to pack the hydroexothermic substance all together in a top open vessel into which water can be easily supplied to induce the hydroexothermic reaction. Also, it is favorable that the vessel bottom has such a structure that the hydroexothermic substance is sustained in the vessel while the reaction liquid can be easily flown thereinto.

It is described above that the liquid for hydroexothermic reaction in the reaction equivalent amount is supplied to the hydroexothermic substance within 1 minute. This means that the reaction liquid in an amount sufficient for reacting the whole hydroexothermic substance is supplied within 1 minute after the breakage of the container holding the liquid. In other words, the reaction liquid in the equivalent amount for hydroexothermic reaction is supplied within 1 minute to the hydroexothermic substance.

As a result, the reaction occurs within 1 minute (or somewhat later in practice) after the reaction liquid is supplied to the whole hydroexothermic substance. Thus, the whole hydroexothermic substance undergoes heat-evolution within a short period of time. Then the thus evolved heat is transferred to the part to be heated, for example, the bottom of the vessel having the preparation therein.

The total heat value which can be evolved by the hydroexothermic substance relates to the amount of the hydroexothermic substance packed in the vessel. Namely, when water is supplied quickly, the heat value evolved by the hydroexothermic substance in a unit time is increased. As a result, the temperature at the hydroexothermic substance part is elevated and, in its turn, the temperature of the container holding the preparation is also elevated.

In the embodiment of the present invention wherein the reaction liquid is packed in a container and then introduced into a vessel together with the exothermic substance, it is favorable that a large opening is formed when the container holding the liquid therein is broken. With respect to the structure of a self-exothermic vessel wherein the hydroexothermic substance is contained, a water-absorbing substance such as filter paper is usually adhered to the bottom of the self-exothermic vessel so as to facilitate water absorption. When this filter paper prevents water from flowing into the self-exothermic vessel, it is necessary to use, for example, a porous paper sheet or a thin plate provided with a number of pores allowing water to pass therethrough. Alternatively, other water-absorbing materials such as nonwoven fabric may be used therefor. It is also possible to add a surfactant to the water-absorbing material so as to enhance the water absorptivity.

To supply the reaction liquid in the amount needed in the reaction (or the total amount when it is preliminarily quantitated) to the hydroexothermic substance in the case wherein the reaction liquid is packed in a container and then introduced into a vessel together with the exothermic substance, it is necessary that the liquid is quickly discharged from the container upon the breakage and supplied to the hydroexothermic substance in such an amount as attaining the hydroexothermic reaction equivalence. It is therefore favorable that a large opening is formed at the breakage of the container holding the liquid. Thus, it is recommended that either a large hole or plural holes are formed upon the breakage of the container of the liquid.

As the liquid stabilizer to be contained in the reaction liquid, use can be made of substances which neither prevent the evaporation of the chemical nor lower the reactivity of water with the exothermic substance, can prevent water from putrefaction during storage and do not deteriorate the fluidity of water. As examples of such substances, citation maybe made of liquid stabilizers capable of elevating the temperature of the part to be heated (i.e., the vessel containing the thermal evaporation preparation) to 300° C. or more (preferably 300 to 400° C.) within 100 seconds, preferably 40 to 100 seconds, after the initiation of the absorption of water by the hydroexothermic substance. Thus, the temperature can be quickly elevated by the heat evolved after the initiation of the water supply and, in its turn, the temperature of the preparation can be quickly elevated too. As a result, the vaporized amount of the chemical is increased, which enables more efficient evaporation of the chemical.

Examples of the liquid stabilizer include acids, quaternary ammonium compounds, amphoteric surfactants, anionic surfactants, inorganic chlorine compounds, organic chlorine compounds and the like.

Among these liquid stabilizers, acids in the form of salts thereof have high solubility and relatively high concentration in practical use. As examples thereof, sodium dehydroacetate, sodium benzoate and potassium sorbate may be exemplified.

Some of the quaternary ammonium compounds fall within the category of surfactants due to the properties thereof. Examples thereof include benzalkonium chloride, benzethonium chloride and cetylpyridinium chloride.

As the amphoteric surfactants, alkyldiaminoethylglycine hydrochloride, etc., are exemplified.

As the anionic surfactants, sodium lauryl sulfate, etc., are exemplified.

Examples of the inorganic chlorine compounds include calcium hypochlorite, sodium hypochlorite and chlorine dioxide.

As the organic chlorine compounds, trichloroisocyanuric acid, etc., are exemplified.

In addition, use may be also made of chlorohexydine gluconate, phenoxy ethanol, etc.

Among all, it is preferable that the liquid stabilizer is at least one member selected from the group consisting of alcohols, benzethonium chloride, benzalkonium chloride, sucrose, alkyldiaminoethylglycine hydrochloride, chlorohexydine gluconate, cetylpyridinium chloride, sodium lauryl sulfate, sodium dehydroacetate, chlorinated isocyanuric acid and refined chloride of lime.

As the alcohols, use can be made of methanol, ethanol, isopropyl alcohol, etc.

The amount of the liquid stabilizer as described above may be appropriately controlled depending on the type of the liquid stabilizer. Now, use of alcohols will be illustrated, since they are to be used in a larger amount as compared with other liquid stabilizers. A liquid stabilizer other than alcohols may be used in an effective amount, for example, from 0.0001 to 10 w/v % (the term "w/v %" means weight/volume %), based on water.

In contrast, an alcohol may be used as the liquid stabilizer in an amount of 5 to 50 v/v %, preferably 10 to 30 v/v % (the term "v/v %" means volume/volume %), based on water.

When the liquid stabilizer evolves an acid gas when heated, it may be neutralized by adding a compound evolving a basic gas upon heating (calcium hydroxide, etc.).

Now, preferable embodiments of the device for the thermal evaporation of chemicals as described above will be illustrated by the attached drawings.

In FIG. 1, a self-exothermic device 1 is provided with a bottomed cylindrical external vessel 2. A hydroexothermic substance A is packed in the part from the bottom to the side of this external vessel 2. This external vessel 2 is a can made of a metal. As the hydroexothermic substance A, quick lime (calcium oxide) is employed. The external vessel 2 has water-permeable holes covered with a water-permeable material. In this case, a nonwoven fabric sheet 3 is employed as the water-permeable material. When the nonwoven fabric sheet is impregnated with a surfactant, the water-permeability is improved.

Inner space of the external vessel 1 is divided into 2 rooms by a partition member 4. The side wall of the partition member 4 is located around the peripheral wall (i.e., the external peripheral wall) of the external vessel 2 in the radial direction. In this case, the side wall and the external peripheral wall are located concentrically. One end (the top end in FIG. 1) of the partition member 4 is in contact with a covering member 6, while the other end (the bottom end in FIG. 1) is connected to the bottom of the partition member 4. The bottom plate of the partition member 4 has an almost hollow hemispherical shape. In this case, the hydroexothermic substance A is packed in the space between the external peripheral wall and the side wall of the partition member 4 and the space between the nonwoven fabric sheet 3 and the bottom plate of the partition member 4. The substance B to be heated is packed in the space between the cover member 6 and the partition member 4. This space is connected to the outside via air-permeable holes provided in a resin film 7.

FIG. 3 shows another embodiment of a self-exothermic device 1. In this case, a hydroexothermic substance A is contained in the bottom of an external vessel 2 which is made of paper.

The inner space of the external vessel 2 is divided into a first space located lower (serving as a container for the exothermic substance) and a second space located upper (serving as a container for the thermal evaporation preparation) by a disc partition member 4 provided in the direction orthogonal to the peripheral wall of the external vessel 2, i.e., horizontally in FIG. 3. In this case, the lower space is shut up to the outside by the partition member 4 which is fixed to the periphery. The substance to be heated, i.e., the thermal evaporation preparation B according to the present invention is placed on the partition member 4, i.e., in the upper space.

FIG. 2 is a perspective view of a self-exothermic device 1 which is packed in a vessel 20. As FIG. 2 shows, the top opening of the external vessel 20 is covered with a cover member 6. The cover member 6 is provided with plural holes covered with a hot-melt resin film 7 which is molten by heating and provides openings in using. Air-permeable holes 8 are formed on this resin film 7. This self-exothermic device 1 can be stored or used in the state of being packed in the vessel 20. An exothermic reaction liquid W is held in a container which can be packed in the vessel 2 together with the self-exothermic device 1 as described above. In the embodiment shown in FIG. 2, the container 21 holding the exothermic reaction liquid W therein is a bag which is put into a space between the self-exothermic device 1 and the vessel 20. The container 21 may be either a bag as in the above case or a solid vessel. It may be made of waterproof paper, resins or metals. It is preferable that this container is a bag made of a film (aluminum foil, nylon, moisture-proof film etc.) which can be torn without resort to scissors or a film having a cut end for tearing at one end.

As an embodiment other than the container 21 as described above, a space is preliminarily formed in the vessel 20 and the exothermic reaction liquid, which is optionally packed in a container, is put in the space. To evaporate the chemical by using this device, the exothermic reaction liquid provided in the vessel 20 may be reacted with the exothermic substance by externally handling. For example, the container holding the exothermic reaction liquid packed in the vessel 20 is broken so as to allow the liquid contained therein to flow into the vessel 20. Thus, the liquid W comes in contact with the exothermic substance A, as shown in FIG. 1.

Alternatively, the container 20 holding the exothermic liquid W as shown in FIG. 2 is broken and the exothermic liquid W contained therein is introduced into a vacant vessel 20. Next, the self-exothermic device 1 is introduced into the vessel 20 holding the exothermic reaction liquid W, thereby initiating the exothermic reaction.

Because of being excellent in the evaporability, the thermal evaporation preparations according to the present invention are usable in rooms in houses and buildings or various vehicles. In particular, these preparations can be appropriately employed in vehicles such as automobiles, airplanes and trains having with metal goods and electrical wiring or rooms equipped with computers, ornamental plants, family Buddhist altars, etc.

In the present invention, the hydroexothermic reaction liquid contains the liquid stabilizer which is capable of elevating the temperature at the part to be heated to 300° C. or more within 100 seconds after the initiation of water absorption by the hydroexothermic substance. Thus, temperature can be quickly elevated due to the heat evolved after the initiation of the water absorption. As a result, the temperature of the chemical can be quickly elevated too and attain a high maximum temperature. Owing to this construction, the chemical can be efficiently evaporated in a large amount while eliminating the waste in the vessel. Thus, the chemical can be applied to the desired space at the highest efficiency. Moreover, the evaporation at a high reproducibility can be repeated by using the same evaporation device, which ensures the achievement of a highly reliable and stable evaporation effect.

BEST MODE FOR THE EMBODIMENT OF THE INVENTION

The present invention will be described in greater detail by the following Examples, but is should be understood that the invention is not construed as being limited thereto.

The following samples (1), (2) and (3) were employed.
<Sample (1) (Invention)>

3.85 g of the active ingredient, 3.65 g of butyl p-hydroxybenzoate (m.p.: 69–72° C.), 0.2 g of p-chloro-m-xylenol (m.p.: 114° C.), 0.2 g of a plant essential oil (tea leaf extract: liquid), 0.05 g of corn starch and 0.7 g of sorbitol (m.p.: 135–137° C.) were uniformly mixed together and the obtained mixture was processed with a granulating machine to give 5 g of a granular preparation having a particle diameter of 3 mm.

5 g of this granular preparation was packed in a vessel and the vessel containing this preparation was introduced into a container of a thermal evaporation device provided with the hydroexothermic system of a heating (exothermic) temperature of about 300 to 400° C.

<Sample (2) (Comparison)>

This sample contained the same active ingredient as that of the above sample (1) together with 0.8 g of an inorganic substance (sodium carbonate) not melting at 50 to 300° C. Thus, the preparation was not molten into a liquid as a whole even at 50 to 300° C. As a heating means, the hydroexothermic system of a heating (exothermic) temperature of about 300 to 400° C. was employed in this thermal evaporation device too.

Figure 1:
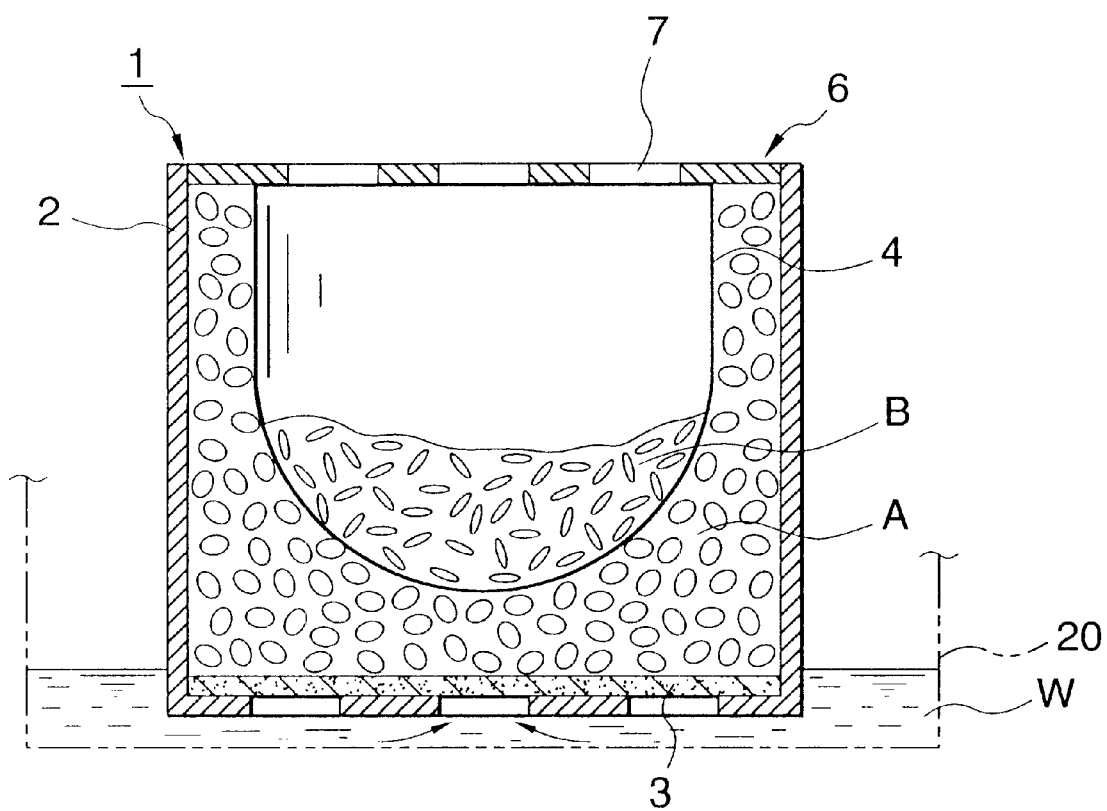
FIG. 1 is a schematic sectional view of a device which can be appropriately employed in the present invention.
Figure 2:
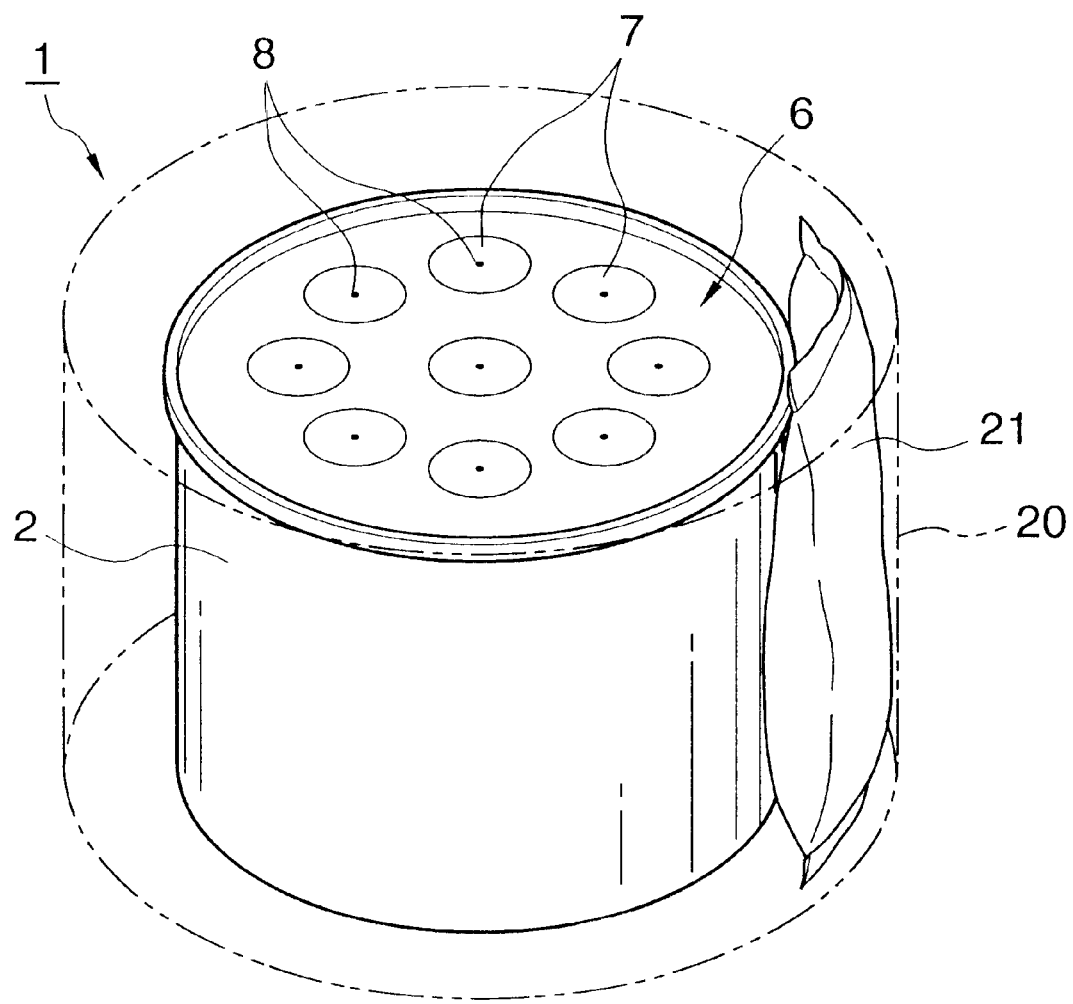
FIG. 2 is a perspective view of a device which can be appropriately employed in the present invention.
Figure 3:
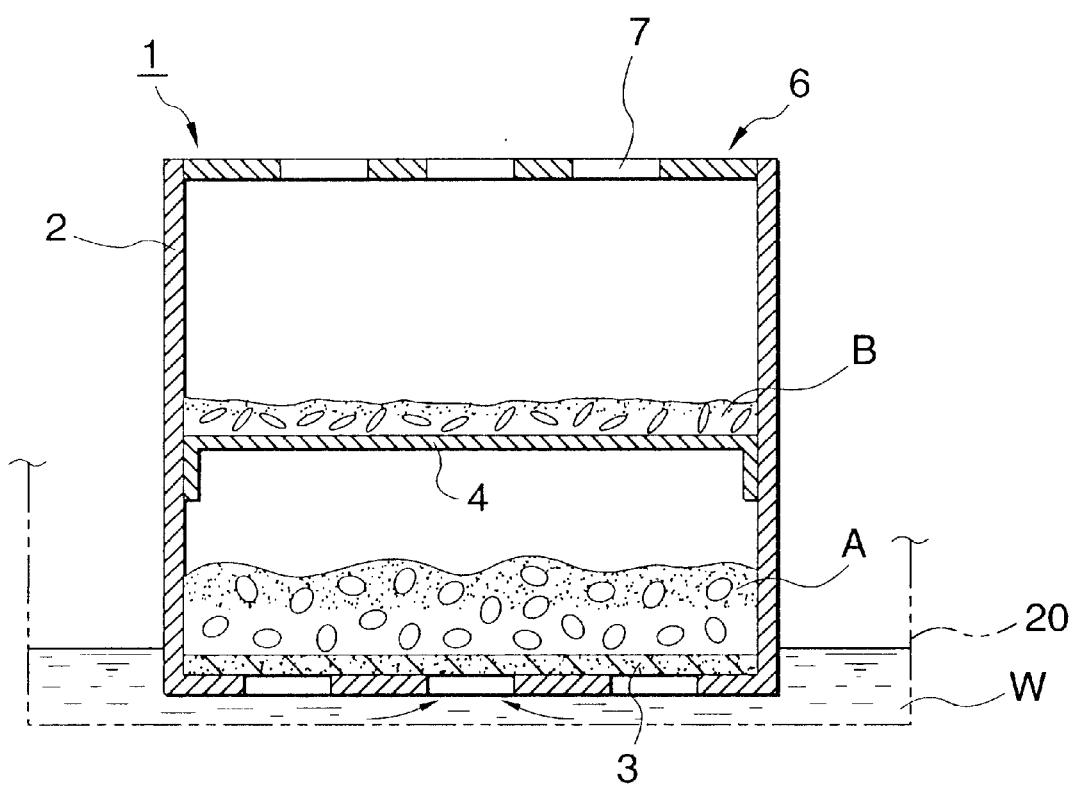
FIG. 3 is a schematic sectional view of a device of another embodiment which can be appropriately employed in the present invention.

In each of the above samples (1) and (2), the device as shown in FIGS. 1 and 2 was employed as the thermal evaporation device. 65 g of calcium oxide was employed as the hydroexothermic substance, while 23 ml of water was employed as the exothermic reaction liquid. More particularly speaking, the container 21 holding therein the exothermic reaction liquid (i.e., water) was torn and the water was poured into the vessel 20. Then, hydroexothermic substance A (i.e., calcium oxide) and the thermal evaporation preparation (i.e., the sample (1) or (2)) were fed thereinto thereby initiating the exothermic reaction/evaporation.

<Sample (3) (Reference)>

Although this sample contained the same active ingredient as that of the above sample (1), it was in the form of an aerosol preparation of the full injection type.

The characteristics of these samples (1) to (3) were examined. Each sample was heated or injected and thus the active ingredient was evaporated. When heated to 300° C., the granular preparation of the sample (1) was molten as a whole into a liquid (melting time: 5 minutes). On the other hand, the preparation of the sample (2) was not molten as a whole at 300 to 400° C. (heating time: 5 minutes) and solid matters remained.

The particle diameters of the evaporated particles were measured with an Andersen sampler (manufactured by Tokyo Daimukku K.K.). More particularly speaking, each sample was put into a peat grady chamber (180 cm×180 cm×180 cm) and, 5 minutes after the initiation of the evaporation, the particles evaporated into the chamber were collected and measured in the diameter with the Andersen sampler.

The results are shown in Table 1. Table 2 shows the median particle diameter, distribution range and the ratio of the distribution range to the median particle diameter.

TABLE 1

| Sample No. | Distribution ratio (%) of particle diameter ($\mu$m) | | | | | | | | |
|---|---|---|---|---|---|---|---|---|---|
| | <0.2 | 0.2–0.5 | 0.5–1.0 | 1.0–1.5 | 1.5–3.5 | 3.5–5.5 | 5.5–7.5 | 7.5–9.5 | 9.5< |
| 1 (invention) | 7 | 13 | 16 | 11.5 | 22.5 | 10 | 5.2 | 3.8 | 11 |
| 2 (comparison) | 0.15 | 3.4 | 15.0 | 17.5 | 41.0 | 14.0 | 5.0 | 2.0 | 2.0 |
| 3 (reference) | 0.01 | 0.1 | 3.4 | 11.5 | 35.0 | 28.0 | 10.0 | 6.0 | 6.0 |

TABLE 2

| Sample No. | Median particle diameter ($\mu$m) | Distribution range* | Ratio of distribution range to median particle diameter |
|---|---|---|---|
| 1 (invention) | 1.7 | 0.40–7.0 | ¼–4 |
| 2 | 2.0 | 0.9–4.3 | ½–2 |
| 3 | 3.5 | 1.75–6.7 | ½–2 |

*Particle diameter range involving about 68% of the particles having the median particle diameter as the center (statistical distribution).

EXMPLE 1

Mildewproofing/antibacterial Test (1) Test Method

To collect molds and bacteria inhabiting in the internal circuit of an automotive air conditioner, the engine was started while shutting the doors and windows of the automobile. The air conditioner was switched off and operated in the ventilation mode. A potato dextrose agar medium (contained in a plastic Petri dish of 9 cm in diameter) was located in parallel to the vent of the air conditioner for 2 minutes (i.e., exposed to the air fed from the air conditioner for 2 minutes). The microorganisms thus collected were incubated in a thermostat at 25° C. for 5 days to thereby confirm the growth of molds and bacteria.

In the automobile in which the growth of molds and bacteria had been thus proved, the above-described three samples were used as defined. After the treatments, the molds and bacteria were collected by the same method as described above and the surviving conditions of the molds and bacteria were compared before and after the treatments with the samples.

(2) Test Results

The mildewproofing/antibacterial effects were evaluated in 3 grades based on the following criteria, on the basis of the conditions of the molds and bacteria before the treatment.

++: Completely inhibiting the growth of molds and bacteria.

+: Inhibiting the growth of molds and bacteria.

±: Scarcely inhibiting the growth of molds and bacteria.

The results are shown in Table 3.

TABLE 3

| | Mildewproofing/antibacterial effect | | |
|---|---|---|---|
| Sample | 1 | 2 | 3 |
| Mildewproofing/antibacterial effect | ++ | + | ± |

EXAMPLE 2

Deodorizing Test (1) Test Method (Sensory Test Method)

A Petri dish containing a sheet of No. 2 filter paper (diameter: 90 mm) impregnated with 0.5 ml of an imitated moldy smell solution (manufactured by Hasegawa Perfume K.K.) or a fish per se (for testing a fish smell) was placed at the center of the floor of a sensory test box of 2.2 m³ in capacity (0.85 m×1.35 m×1.95 m in height). On the other hand, a tobacco smell was tested by the same method as that of the moldy smell but using 1 ml of an imitated tobacco smell solution (manufactured by Ogawa Perfume K.K.).

The three samples as described above (each containing no perfume) were fully evaporated or injected on the floor of these sensory test boxes. After allowing to stand for 15 minutes, inlet fans and ventilation fans were operated in each box for 10 minutes. After switching off the fans, the intensity of the imitated moldy smell or fishy smell was sensorily evaluated in the following manner.

(2) Test Results

By using an untreated lot as a control, the masking effects (deodorizing effects) were evaluated in 5 grades on the basis of the following criteria.

1: No masking effect (comparable to the control lot).
2: Somewhat relieved bad smell as compared with the control lot.
3: Noticeable but very weak bad smell.
4: Slight bad smell.
5: Very high masking effect (no bad smell).

The thermal evaporation preparation according to the present invention (the sample 1) exerted very excellent masking effects on the moldy smell and the fishy smell. Table 4 shows the results on the moldy smell and the fishy smell. Moreover, the tobacco smell was tested in the same manner. As a result, the sample according to the present invention showed the most favorable result.

TABLE 4

| | Masking effect | | |
|---|---|---|---|
| Sample | 1 | 2 | 3 |
| Moldy smell | 5 | 3 | 4 |
| Fishy smell | 5 | 2 | 4 |

The results of Examples 1 and 2 as described above clearly show that the thermal evaporation preparation or method of thermal evaporation according to the present invention is superior in the evaporation performance of the chemical (for example, mildewproofing, antibacterial and deodorizing effects) to the comparative thermal evaporation preparation (the sample (2)) and the aerosol preparation of the full injection type (the sample (3)).

EXAMPLE 3

By using the above-described sample (1), an experiment was performed to evaporate the chemical as described above, provided that the exothermic reaction liquids of the following compositions were used:

Sample 1A 0.2 w/v % aqueous solution of benzethonium chloride;

Sample 2A 0.2 w/v % aqueous solution of sucrose;

Sample 3A 0.2 w/v % aqueous solution of alkyldiaminoethylglycine hydrochloride;

Sample 1B 1 w/v % aqueous solution of benzethonium chloride;

Sample 2B 1 w/v % aqueous solution of sucrose;

Sample 3B 1.0 w/v % aqueous solution of alkyldiaminoethylglycine hydrochloride; and Sample 4 water free from any additive.

Test and Results

The temperature at the part to be heated was measured with a temperature sensor being in contact with the center of the bottom plate of the partition member 4 shown in FIG. 1. Thus changes in the exothermic temperature with the passage of time (second) after the initiation of the water absorption were monitored.

Figure 4:
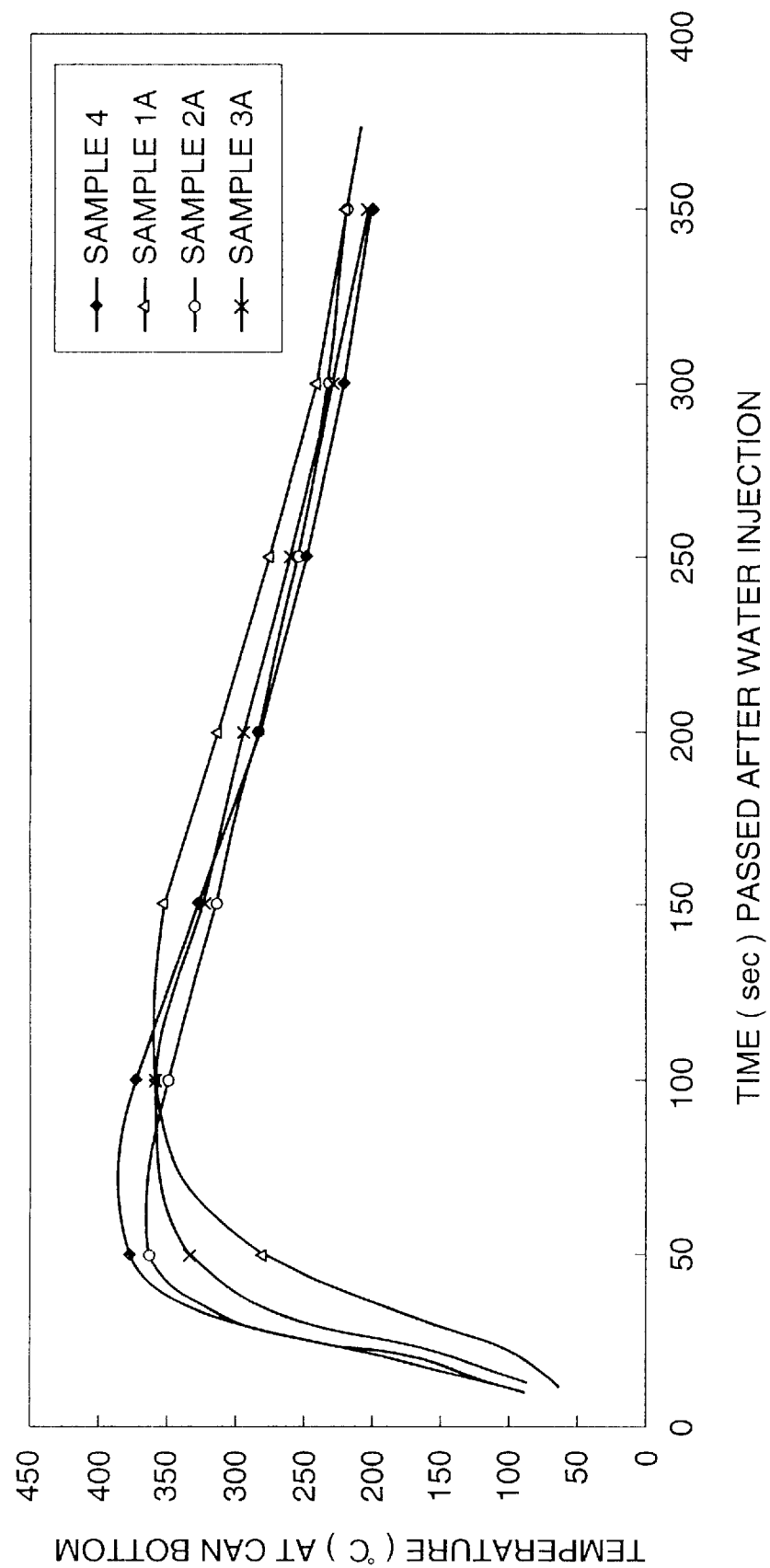
FIG. 4 is a graph which shows the relation between time passed after the injection of a hydroexothermic reaction liquid, which is a 0.2% by weight aqueous solution of a liquid stabilizer, and the temperature of the hydroexothermic substance.
Figure 5:
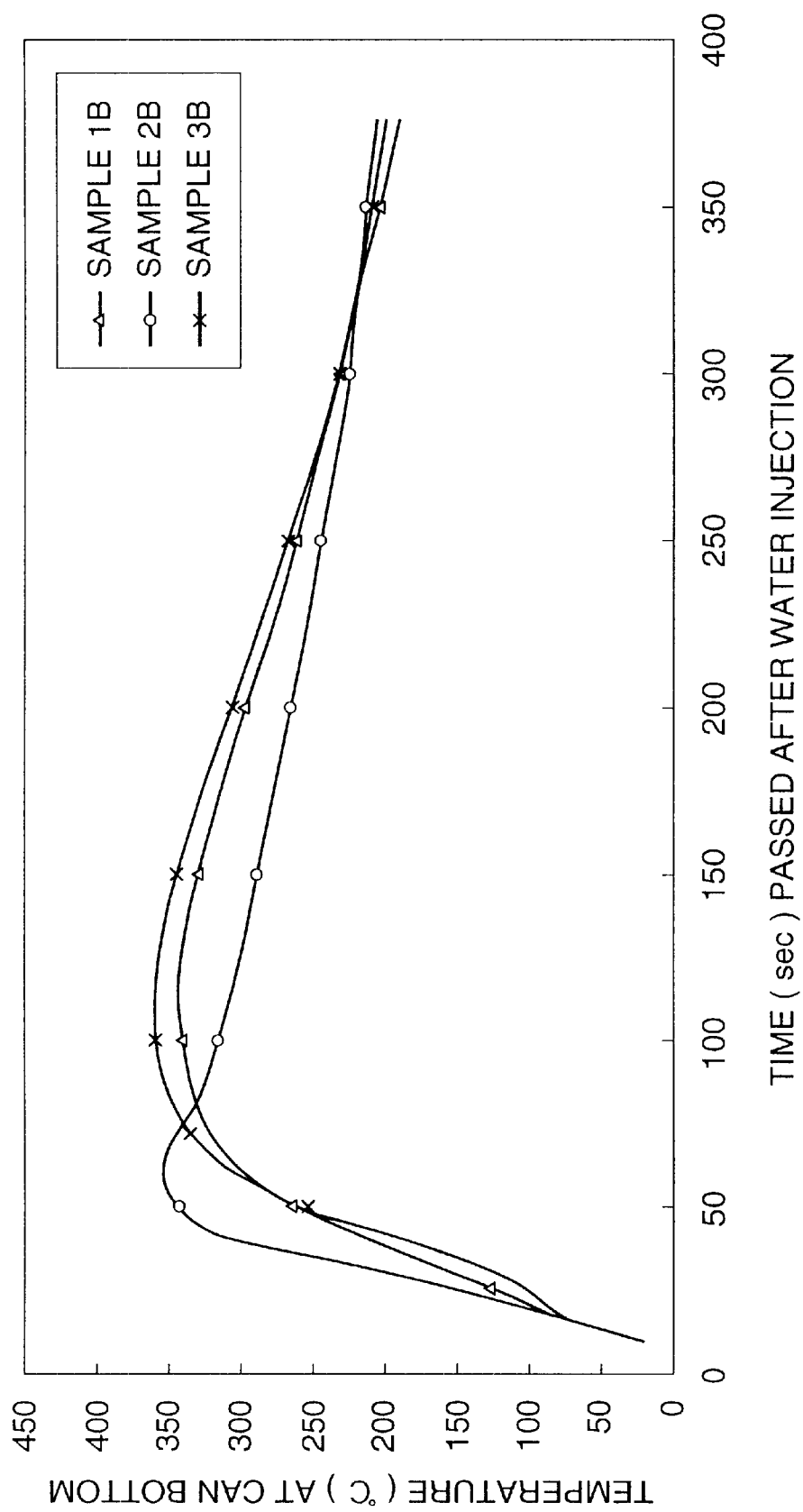
FIG. 5 is a graph which shows the relation between time passed after the injection of a hydroexothermic reaction liquid, which is a 1% by weight aqueous solution of a liquid stabilizer, and the temperature of the hydroexothermic substance.

FIG. 4 shows the relations between the time after the water injection and the exothermic temperature of the samples 1A, 2A, 3A and 4, while FIG. 5 shows the relations between the time after the water injection and the exothermic temperature of the samples 1B, 2B and 3B. Each value is the average of the data obtained by repeating the procedure thrice.

Table 5 shows the relation of each sample between the maximum exothermic temperature at the can bottom and the time required for attaining this temperature after initiation of the water injection.

TABLE 5

| Sample | Time (sec) for attaining 300° C. | Maximum exothermic temperature (° C.) | Time (sec) for attaining the maximum exothermic temperature |
|---|---|---|---|
| 1A | 58 | 360 | 110 |
| 2A | 30 | 365 | 60 |
| 3A | 40 | 355 | 80 |
| 4 | 30 | 380 | 80 |
| 1B | 66 | 340 | 120 |
| 2B | 30 | 350 | 60 |
| 3B | 70 | 360 | 110 |

These results indicates that the samples 1A, 2A and 3A all satisfy the requirement of attaining the maximum exothermic temperature exceeding 300° C. within 100 seconds (i.e., about 30 to 58 seconds in practice). Also, the samples 1B, 2B and 3B all satisfy the requirement of attaining the maximum exothermic temperature exceeding 300° C. within 100 seconds (i.e., about 30 to 70 seconds in practice).

Accordingly, it has been proved that excellent evaporability can be established by using the hydroexothermic system and employing the above-described ones as the reaction liquid in the present invention.

EXAMPLE 4

Now, formulation examples of the thermal evaporation preparation of the present invention will be given, though the present invention is not restricted thereto.

| Formulation Example 1: | |
|---|---|
| Butyl p-oxybenzoate | 2.0 g |
| isopropylmethyl phenol | 0.4 g |
| lauryl methacrylate | 0.2 g |
| 1,2,3-benzotriazole | 0.2 g |
| sorbitol | 1.9 g |
| starch | 0.1 g |
| perfume (lemon type) | 0.2 g |
| total | 5.0 g. |
| Formulation Example 2: | |
| Butyl p-oxybenzoate | 2.4 g |
| isopropylmethyl phenol | 0.4 g |
| lauryl methacrylate | 0.2 g |
| 1,2,3-benzotriazole | 0.2 g |
| sorbitol | 0.5 g |
| starch | 0.1 g |
| corn starch | 0.5 g |
| sodium hydrogencarbonate | 0.5 g |
| perfume (green type) | 0.2 g |
| total | 5.0 g. |
| Formulation Example 3: | |
| Butyl p-oxybenzoate | 2.0 g |
| isopropylmethyl phenol | 0.4 g |
| lauryl methacrylate | 0.2 g |
| 1,2,3-benzotriazole | 0.2 g |
| sorbitol | 0.5 g |
| starch | 0.1 g |
| perfume (citrus type) | 0.2 g |
| total | 3.6 g. |

INDUSTRIAL APPLICABILITY

The thermal evaporation preparations according to the present invention are superior to the conventional thermal evaporation preparations or aerosol preparations in the evaporation and diffusion of the chemical. Also, these thermal evaporation preparations of the present invention would not cause rusting of metal goods or electrical wiring and exert no harmful influence on ornamental plants.

Owing to these characteristics, the thermal evaporation preparations of the present invention can be appropriately used in vehicles such as automobiles, airplanes and trains and placed provided with many metal goods or ornamental plants.

What is claimed is:

1. A thermal evaporation preparation, wherein said preparation is in the form of a solid at ordinary temperature but molten by heating using heat evolved by a hydroexothermic reaction between a hydroexothermic substance and a liquid for the hydroexothermic reaction to become a liquid as a whole, and a chemical employed as the active ingredient is evaporated from the ingredients of the preparation thus liquefied by heating.

2. A thermal evaporation preparation, wherein said preparation is in the form of a solid at ordinary temperature but molten by heating into a liquid as a whole, and a chemical employed as the active ingredient is evaporated from the ingredients of the preparation thus liquefied by heating, and
   wherein from said preparation liquefied by heating, particles having a median particle diameter ($\mu$) of 1 to 2 $\mu$m and an evaporated particle diameter distribution giving $\mu+\alpha$ (wherein $\alpha$ represents the standard deviation) of $4\mu$ (i.e., 4 times as much as the median particle diameter) and $\mu-\alpha$ of 1/4 (i.e., 1/4 times as much as the median particle diameter) are evaporated.

3. The thermal evaporation preparation as claimed in claim 1 or 2, wherein all of the ingredients of the preparation have each a melting point falling within a range of from 50 to 300° C.

4. A method of thermal evaporating a chemical from a thermal evaporating preparation which is in the form of a solid at ordinary temperature but molten by heating into a liquid as a whole, and a chemical employed as the active ingredient is evaporated from the ingredients of the preparation thus liquefied by heating, comprising the following steps:
   the step of heating the thermal evaporation preparation with a heating means and melting said preparation into a liquid as a whole; and
   the step of evaporating the chemical employed as the active ingredient from the ingredients of the thus liquefied preparation, wherein said heating means is a means with the use of heat evolution caused by a hydroexothermic reaction between a hydroexothermic substance and a liquid for the hydroexothermic reaction.

5. A method of thermal evaporating a chemical in which a thermal evaporation preparation which is in the form of a solid at ordinary temperature is molten by heating using heat evolved by a hydroexothermic reaction between a hydroexothermic substance and a liquid for the hydroexothermic reaction to become a liquid as a whole, to thereby evaporate the chemical used as the active ingredient in the preparation, wherein said liquid for the hydroexothermic reaction is supplied so as to elevate the temperature at the part to be heated to 300° C. or more within 100 seconds after the initiation of water absorption by said hydroexothermic substance.

6. A method of thermal evaporating a chemical in which a thermal evaporation preparation is heated by using heat evolved by a hydroexothermic reaction between a hydroexothermic substance and a liquid for the hydroexothermic reaction to thereby evaporate the chemical used as the active ingredient in the preparation, wherein said liquid for the hydroexothermic reaction is supplied so as to be capable of elevating the temperature at the part to be heated to 300° C. or more within 100 seconds after the initiation of water absorption by said hydroexothermic substance, and wherein said liquid for the hydroexothermic reaction comprises a liquid stabilizer capable of elevating the temperature at the part to be heated to 300° C. or more within 100 seconds after the initiation of water absorption by said hydroexothermic substance.

7. The method of thermal evaporating a chemical as claimed in claim 6, wherein said liquid stabilizer is at least one member selected from the group consisting of alcohols, benzethonium chloride, benzalkonium chloride, sucrose, alkyldiaminoethylglycine hydrochloride, chlorohexydine gluconate, cetylpyridinium chloride, sodium lauryl sulfate, sodium dehydroacetate, chlorinated isocyanuric acid and refined chloride of lime.

8. A method of thermal evaporating a chemical from a thermal evaporation preparation which is in the form of a solid at ordinary temperature but molten by heating into a liquid as a whole, and a chemical employed as the active ingredient is evaporated from the ingredients of the-preparation thus liquefied by heating, comprising the following steps:
   the step of heating the thermal evaporation preparation with a heating means and melting said preparation into a liquid as a whole; and
   the step of evaporating the chemical employed as the active ingredient from the ingredients of the thus liquefied preparation, and
   said step of evaporating a chemical is one in which the chemical used as the active ingredient is evaporated from the ingredients of said liquefied preparation as particles having a median particle diameter ($\mu$) of 1 to 2 $\mu$m and an evaporated particle diameter distribution giving $\mu+\alpha$ (wherein $\alpha$ represents the standard deviation) of $4\mu$ (i.e., 4 times as much as the median particle diameter) and $\mu-\alpha$ of 1/4 (i.e., 1/4 times as much as the median particle diameter).

9. A method of thermal evaporating a chemical in which a thermal evaporation preparation which is in the form of a solid at ordinary temperature is molten by heating using heat evolved by a hydroexothermic reaction between a hydroexothermic substance and a liquid for the hydroexothermic reaction to become a liquid as a whole, to thereby evaporate the chemical used as the active ingredient in the preparation, wherein said liquid for the hydroexothermic reaction is supplied so as to elevate the temperature at the part to be heated to 300° C. or more within 100 seconds after the initiation of water injection by said hydroexothermic substance.

* * * * *